United States Patent [19]

Palencia Adrubau et al.

[11] Patent Number: 5,081,319
[45] Date of Patent: Jan. 14, 1992

[54] PROCESS FOR THE PREPARATION OF 1,1-BIS(4-CHLOROPHENYL)-2,2,2-TRICHLOROETHANOL

[75] Inventors: Jaime Palencia Adrubau; Jaume Castellà Solà, both of Badalona, Spain

[73] Assignee: Sociedad Española de Desarrollos Quimicos S.A., Barcelona, Spain

[21] Appl. No.: 555,066

[22] Filed: Jul. 18, 1990

[30] Foreign Application Priority Data

Jul. 18, 1989 [ES] Spain .................... 8902527
Jun. 27, 1990 [ES] Spain .................... 9001766

[51] Int. Cl.$^5$ .................... C07C 29/74; C07C 29/86
[52] U.S. Cl. .................... 568/810; 568/809; 568/812
[58] Field of Search .................... 568/811, 812, 809, 810

[56] References Cited

U.S. PATENT DOCUMENTS 2,812,280 11/1957 Wilson et al. .................... 568/810
2,812,362 11/1957 Wilson et al. .................... 568/810
4,705,902 11/1987 Nichols et al. .................... 568/812
4,778,568 10/1988 Schneider et al. .................... 568/812

FOREIGN PATENT DOCUMENTS

0383054 8/1990 European Pat. Off. .................... 568/809
8603248 11/1988 Spain .................... 568/810
8803818 12/1988 Spain .................... 568/810
831421 4/1960 United Kingdom .................... 568/810

Primary Examiner—Werren B. Lone
Attorney, Agent, or Firm—Scully, Scott, Murphy & Presser

[57] ABSTRACT

1,1-bis(4-chlorophenyl)-2,2,2-trichloroethanol is separated from a mixture comprising by way of the formation of an addition compound between 1,1-bis(4-chlorophenyl)-2,2,2-trichloroethanol and a moderately electron donating compound, preferably selected from a group formed by dimethyl sulphoxide, cyclohexanone, isophoron, pyridine, 1,4-dioxane, acetic acid, acetonitrile and water.

31 Claims, 6 Drawing Sheets

PROCESS FOR THE PREPARATION OF 1,1-BIS(4-CHLOROPHENYL)-2,2,2-TRICHLOROETHANOL

BACKGROUND OF THE INVENTION

1. Field of the Invention

The invention relates to a process for the preparation of 1,1-bis(4-chlorophenyl)-2,2,2-trichloroethanol starting out from a mixture containing 1,1-bis(4-chlorophenyl)-2,2,2-trichloroethanol (p,p'-dicofol) together with at least one compound selected from a first group formed by 1-(4-chlorophenyl)-1-(2-chlorophenyl)-2,2,2-trichloroethanol (o,p'-dicofol); 1-(4-chlorophenyl)-1-(2-chlorophenyl)-2,2,2-trichloroethane (o,p'-DDT); and 1-(4-chlorophenyl)-1-(2-chlorophenyl)-2,2-dichloroethylene (o,p'-DDE).

The starting mixture, apart from the p,p'-dicofol and one or more of the compounds o,p'-dicofol, o,p'-DDT and o,p'-DDE, may obviously contain other compounds. Particularly, said starting mixture may be 1,1-bis(chlorophenyl)-2,2,2-trichloroethanol, also known as technical dicofol.

Dicofol is an acaricide widely used for agricultural purposes in cotton and fruit crops, citrus fruits in particular.

The biologically active product is 1,1-bis(4-chlorophenyl)-2,2,2-trichloroethanol which is to be found in technical dicofol in concentrations of around 70–75 wt %.

2. Prior Art Reference

The preparation of the product (dicofol) is described in U.S. Pat. No. 2,812,280 (Nov. 1957), 2,812,362 (Nov. 1957) and GB 831,421 (March 1960).

The process initially used consisted of photochemical chlorination (Scheme A) of technical DDT, a mixture of various products, but the main components of which are 1,1-bis(4-chlorophenyl)-2,2,2-trichloroethane (p,p'-DDT; approx. 75 wt %) and 1-(4-chlorophenyl)-1-(2-chlorophenyl)-2,2,2-trichloroethane (o,p'-DDT; approx. 20 wt %) by introduction of chlorine gas in DDT under fusion

(A)

which led to the corresponding chlorine derivatives 1,1-bis(4-chlorophenyl)-1,2,2,2-tetrachloroethane (p,p'-ClDDT) and 1-(4-chlorophenyl)-1-(2-chlorophenyl)-1,2,2,2-tetrachloroethane (o,p'-ClDDT).

The chlorination of the o,p'-DDT isomer is incomplete for steric hindrance, leaving a residue of this substance representing a content of about 2 to 7 wt % in the chlorinated end product.

The mixture resulting from the chlorination was subsequently subjected to hydrolysis in an acid medium (Scheme B), consisting of heating to between 120° and 150° C. with an aqueous solution of sulphuric acid and an aryl sulphonic acid.

The dicofol was extracted by dissolution in a solvent and decantation, the organic phase was washed with water and the dicofol was recovered from the solvent by distillation.

The o,p'-DDT was not affected by this hydrolysis and therefore the final content thereof in the technical dicofol was about 2 to 6%.

With a view to reducing this content, the manufacturing process was modified by changing the chlorination by substitution of the DDT by dehydrochlorination first (Scheme C), with a strong alkali, to the corresponding ethylene derivatives, 1,1-bis(4-chlorophenyl)-2,2-dichloroethylene (p,p'-DDE) and 1-(4-chlorophenyl)-1-(2-chlorophenyl)-2,2-dichloroethylene (o,p'-DDE), followed by addition chlorination (Scheme D), also photochemical, to reach the same chlorinated derivative as in the previous case which was subjected to the same acid hydrolysis process.

Nevertheless, the dicofol prepared by any of these processes contains a number of impurities, some of them DDT-related, called DDT.R, among which the following are of known nature.

p,p'-DDT
o,p'-DDT
p,p'-DDD
o,p'-DDD
p,p'-DDE
o,p'-DDE
p,p'-ClDDT
o,p'-ClDDT

Other known impurities contained in dicofol and not consisered as DDT.R are 4,4'-dichlorobenzophenone (p,p'-DCBF), 2,4-dichlorobenzophenone (o,p'-DCBF), 4,4'-dichlorobenzyl (p,p'-DCBZ) and 2,4'-dichlorobenzyl (o,p'-DCBZ).

p,p'-DCBF
o,p'-DCBF
p,p'-DCBZ o,p'-DCBZ

The presence of these impurities implies ecological drawbacks, particularly those related with DDT, generically known as DDT.R, the content of which has been subjected to restrictive specifications to a maximum of 0.1 wt % requiring purification thereof.

U.S. Pat. No. 4,705,902 (Nov. 1987) and Spanish patents 8603248 (16.11.88) and 8802818 (28.07.89) describe purification processes for technical dicofol by liquid-liquid extraction allowing the DDT.R content to be reduced below 0.1 wt %.

Nevertheless, the active principal (1,1-bis(4-chlorophenyl)-2,2,2-trichloroethanol (p,p'-dicofol)) content is still low, between 75-80%, meaning an unnecessary contribution to the environment of additional products in the application thereof.

SUMMARY OF THE INVENTION

The invention discloses a process allowing the preparation of a product having a high 1,1-bis(4-chlorophenyl)-2,2,2-trichloroethanol (p,p'-dicofol) content, even above 98 wt % and a low DDT.R impurity content, even below 0.1 wt %.

The process of the invention is characterised by the formation of an addition compound between 1,1-bis(4-chlorophenyl)-2,2,2-trichloroethanol and a second moderately electron donating compound selected from a second group formed by a hydroxylated substance, an ether, a ketone, a carboxylic acid, a sulphoxide and a nitrogenated derivative, isolation of said addition compound and subsequent decomposition of said addition compound.

Preferably according to the invention, said second group is formed by dimethyl sulphoxide, cyclohexanone, isophoron, pyridine, 1,4-dioxane, acetic acid, acetonitrile and water.

The process of the invention, as said above, is based on the fact, unknown up to the present, that 1,1-bis(4-chlorophenyl)-2,2,2-trichloroethanol (p,p'-dicofol) forms, in view of the special electrophyllic nature of its hydroxyl hydrogen, addition compounds with diverse substances such as water, alcohols, ethers, ketones, carboxylic acids, sulphoxides, sulphones, nitrogenated derivatives, etc.

Some of these addition compounds are easily isolatable crystalline solids responding to the composition and characteristics given in Table 1.

TABLE 1.

| Addition compounds of 1,1-bis(4-chlorophenyl)-2,2,2-trichloroethanol | |
|---|---|
| dimethyl sulphoxide | |
| $(p\text{-}ClC_6H_4)_2C(OH)CCl_3.(CH_3)_2SO$ | mp 93.0–93.5° C. |
| $2(p\text{-}ClC_6H_4)_2C(OH)CCl_3.(CH_3)_2SO$ | mp 103.8–104.7 |
| cyclohexanone | |
| $(p\text{-}ClC_6H_4)_2C(OH)CCl_3.C_6H_{10}O$ | mp 56.0–57.0 |
| isophoron | |
| $(p\text{-}ClC_6H_4)_2C(OH)CCl_3.C_9H_{14}O$ | mp 68.6–69.5 |
| pyridine | |
| $(p\text{-}ClC_6H_4)_2C(OH)CCl_3.C_5H_5N$ | mp 81.8–82.9 |
| 1,4-dioxane | |
| $2(p\text{-}ClC_6H_4)_2C(OH)CCl_3.C_4H_8O_2$ | mp 70.6–71.8 |
| acetic acid | |

TABLE 1.-continued

Addition compounds of 1,1-bis(4-chlorophenyl)-2,2,2-trichloroethanol

| | |
|---|---|
| (p-ClC$_6$H$_4$)$_2$C(OH)CCl$_3$.C$_2$H$_4$O$_2$ acetonitrile | mp 57.4–58.2 |
| (p-ClC$_6$H$_4$)$_2$C(OH)CCl$_3$.C$_2$H$_3$N water | mp unknown |
| (p-ClC$_6$H$_4$)$_2$C(OH)CCl$_3$ × H$_2$O | mp unknown |

These addition compounds may be split into their components either by heat treatment at ordinary or reduced pressure or by washing with water or other hydroxyl derivatives.

The selectivity of formation of these addition compounds, their insolubility in certain solvents and the possibility of decomposing them provide a process by which it is possible to prepare 1,1-bis(4-chlorophenyl)-2,2,2-trichloroethanol, (p,p'-dicofol), from mixtures containing it, with yields in excess of 90%.

The starting mixtures containing 1,1-bis(4-chlorophenyl)-2,2,2-trichloroethanol, (p,p'-dicofol) are preferably those in which it is accompanied mainly by 1-(4-chlorophenyl)-1-(2-chlorophenyl)-2,2,2-trichloroethanol (o,p'-dicofol), i.e. technical dicofol; 1-(4-chlorophenyl)-1-(2-chlorophenyl)-2,2-dichloroethylene (o,p'-DDE); or 1-(4-chlorophenyl)-1-(2-chlorophenyl)-2,2,2-trichloroethane (o,p'-DDT).

When the starting mixture is technical dicofol, variable amounts of 1-(4-chlorophenyl)-1-(2-chlorophenyl)-2,2,2-trichloroethanol (o,p'-dicofol), as such, which vary between 0.1 and 12 wt % in the end product, may be separated jointly with the addition compound of 1,1-bis(4-chlorophenyl)-2,2,2-trichloroethanol (p,p'-dicofol).

The greater or lesser amount of o,p'-dicofol separated out depends on the nature and amount of the solvent used, on the temperature conditions and crystallisation time used and on the amount of crystal seeds present.

According to the invention, the process comprises the steps of: a) forming a solution of the mixture containing 1,1-bis(4-chlorophenyl)-2,2,2-trichloroethanol, (p,p'-dicofol), in a solvent; b) adding the reactant for formation of the addition compound; c) cooling the solution and crystallisation of said addition compound with the optional addition of seed crystals; d) filtering and washing the addition compound and e) recovery of 1,1-bis(4-chlorophenyl)-2,2,2-trichloroethanol.

Optionally and aditionally to the above steps, the separation of 4,4'-dichlorobenzyl (p,p'-DCBZ) by crystallisation and filtration may be inserted among the above steps.

Preferably the solvent used in step a) is an aromatic compound (such as xylene or monochlorobenzene), a halogenated compound (such as carbon tetrachloride), an aliphatic compound (such as hexane, decane), mixtures thereof or a sulphur compound.

As an alternative feature of the invention, said sulphur compound is aqueous dimethyl sulphoxide and steps a) and b) are performed simultaneously.

In a preferred development of the invention, the same solvent as used in step a) is used for the washing.

The reactants used in step b) for the formation of the addition compound are preferably water, ethers (such as dioxane), ketones (such as cyclohexanone and isophoron), carboxylic acids (such as acetic acid), sulphoxides (such as dimethyl sulphoxide), or nitrogenated derivatives (such as pyridine and acetonitrile).

Alternatively, the step e) recovery is conducted by heating the addition compound to a temperature ranging from 20° to 140° C. at a reduced pressure of 1 to 300 mbar, or by treating the addition compound with water at a temperature ranging from 80° to 100° C., or by dissolving said addition compound with water inmiscible organic compounds followed by washing in water.

The invention also relates to the use of 1,1-bis(4-chlorophenyl)-2,2,2-trichloroethanol, which may be prepared according to the process of the invention as an acaricide.

Furthermore, the invention relates to a process for the preparation of the addition compounds of 1,1-bis(4-chlorophenyl)-2,2,2-trichloroethanol, to the addition compounds themselves and to the use thereof as an acaricide and as intermediate for the preparation of 1,1-bis(4-chlorophenyl)-2,2,2-trichloroethanol.

BRIEF DESCRIPTION OF THE DRAWINGS

Reference is made hereinafter to the figures accompanying this specification. These figures show:

FIGS. 1 to 3 are chromatograms produced in high performance liquid chromatography equipment (HPLC); the dwell times in minutes are given in abscissae and the UV absorption intensities are given in ordinates. In particular:

Figure 1:
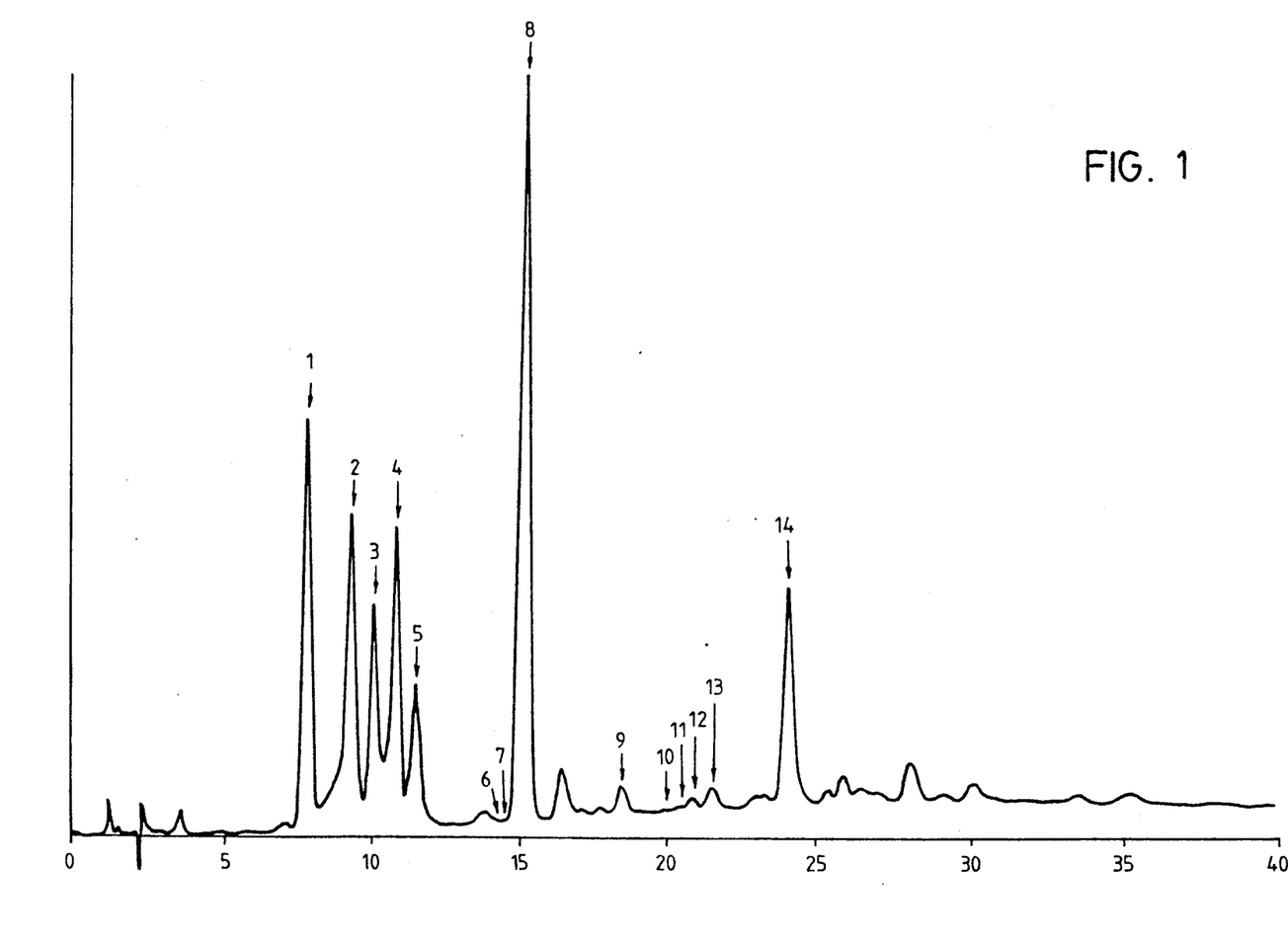
Figure 2:
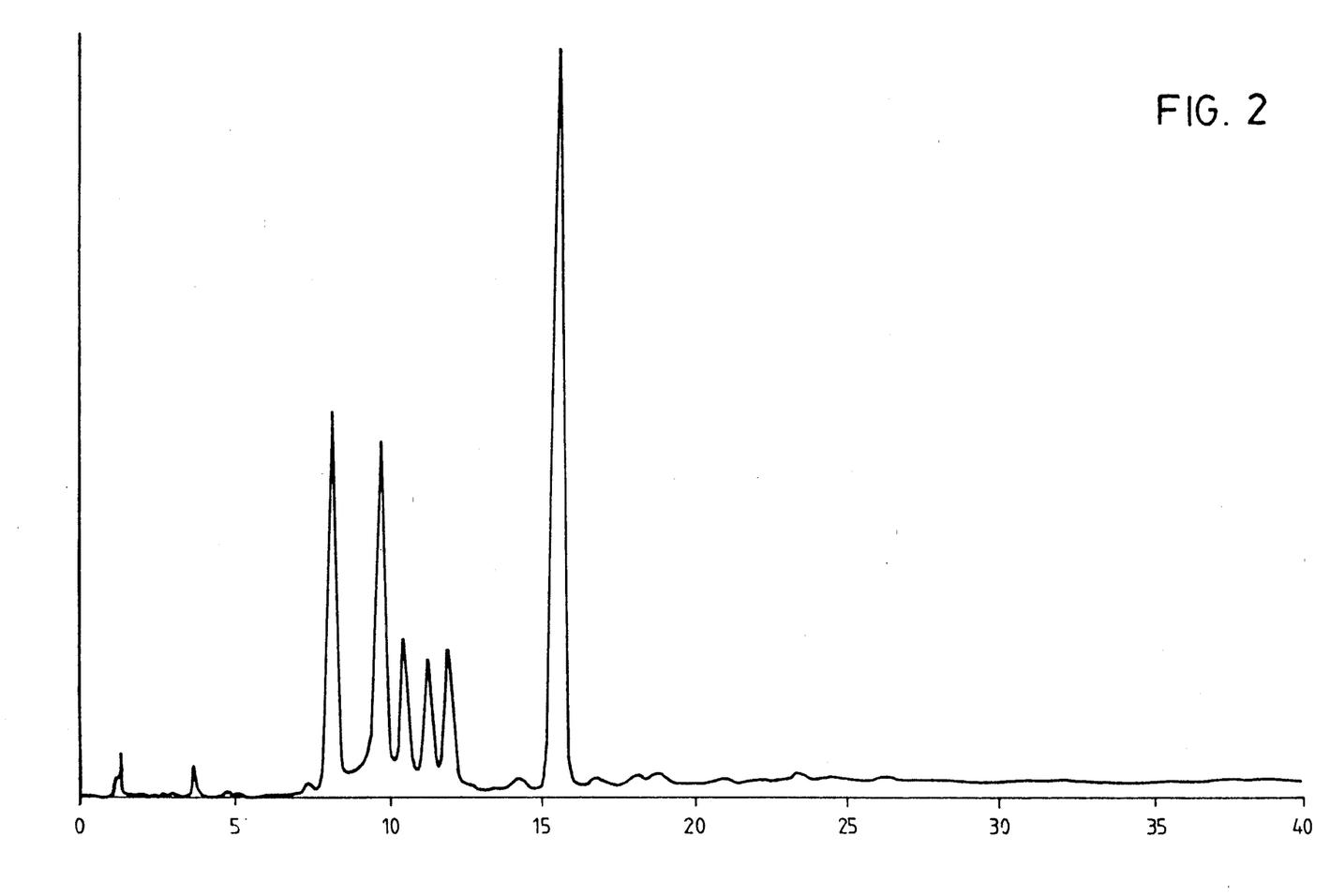
FIG. 2 is an HPLC chromatogram of dicofol purified by liquid-liquid extraction, the composition of which appears in the second column of Table 2.
Figure 3:
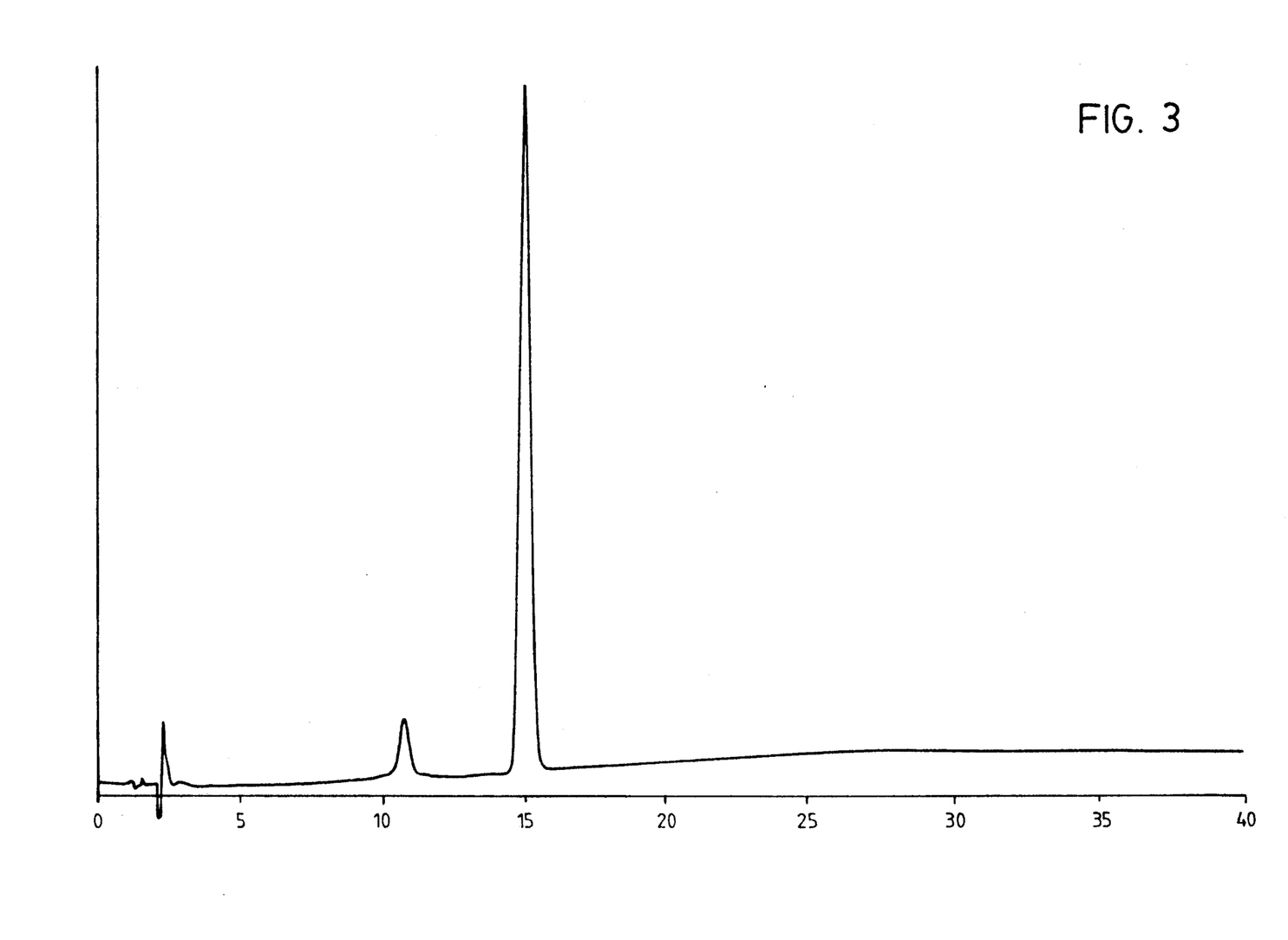
FIG. 3 is an HPLC chromatogram of dicofol purified by the process described herein, the composition of which appears in the third column of Table 2.

The determination and quantification of the impurities contained in the dicofol, referred to hereinabove, may be effected by HPLC. FIG. 1 is the chromatogram of the starting technical dicofol, wherein reference numbers are allocated to the peaks as follows:

| Reference no | Product |
|---|---|
| 1 | o,p'-DCBF |
| 2 | o,p'-DCBZ |
| 3 | p,p'-DCBF |
| 4 | p,p'-DCBZ |
| 5 | o,p'-DICOFOL |
| 6 | p,p'-DDD |
| 7 | o,p'-DDD |
| 8 | p,p'-DICOFOL |
| 9 | o,p'-DDE |
| 10 | p,p'-DDT |
| 11 | o,p'-DDT |
| 12 | p,p'-DDE |
| 13 | o,p'-ClDDT |
| 14 | p,p'-ClDDT |

The composition deduced for this technical dicofol may be seen in the first column of Table 2. Table 2. Comparison of the composition of technical dicofol with that of dicofol purified by liquid-liquid extraction and by the process of the invention.

|  | Starting technical DICOFOL | Purified DICOFOL | |
|---|---|---|---|
|  |  | liquid—liquid extraction | present invention |
| p,p'-DICOFOL | 70.5 wt % | 78.5 wt % | 99.1 wt % |
| o,p'-DICOFOL | 14.7 | 16.9 | 0.6 |
| p,p'-DCBF | 0.4 | 0.25 | <5 ppm |
| o,p'-DCBF | 0.4 | 0.38 | <5 |
| p,p'-DCBZ | 0.7 | 0.30 | 0.2 wt % |
| o,p'-DCBZ | 1.3 | 1.39 | 50 ppm |
| p,p'-DDD | 0.01 | 16 ppm | <5 ppm |
| o,p'-DDD | 0.01 | 5 | <5 |
| p,p'-DDE | 0.03 | 12 | <5 |
| o,p'-DDE | 0.10 | 45 | <5 |
| p,p'-DDT | 0.01 | 5 | <5 |
| o,p'-DDT | 0.01 | 5 | <5 |
| p,p'-ClDDT | 3.5 | 30 | 200 |
| o,p'-ClDDT | 0.6 | 10 | 8 |
| Unidentified | 7.8 | 2 wt % | 0.1 wt % |

Some non-limiting examples of the process of the invention are given herebelow.

EXAMPLE 1

50.0 g of technical dicofol, having a p,p'-dicofol content of 70.5% (column 1, Table 2), were dissolved in a mixture of 26.9 g of xylene and 30.0 g of hexane. 9.0 g of dimethyl sulphoxide were added and the solution was heated for 1 hour at 60° C. It was allowed to crystallise with stirring and cooling to −10° C. It was filtered and washed with the xylene-hexane mixture.

Figure 4:
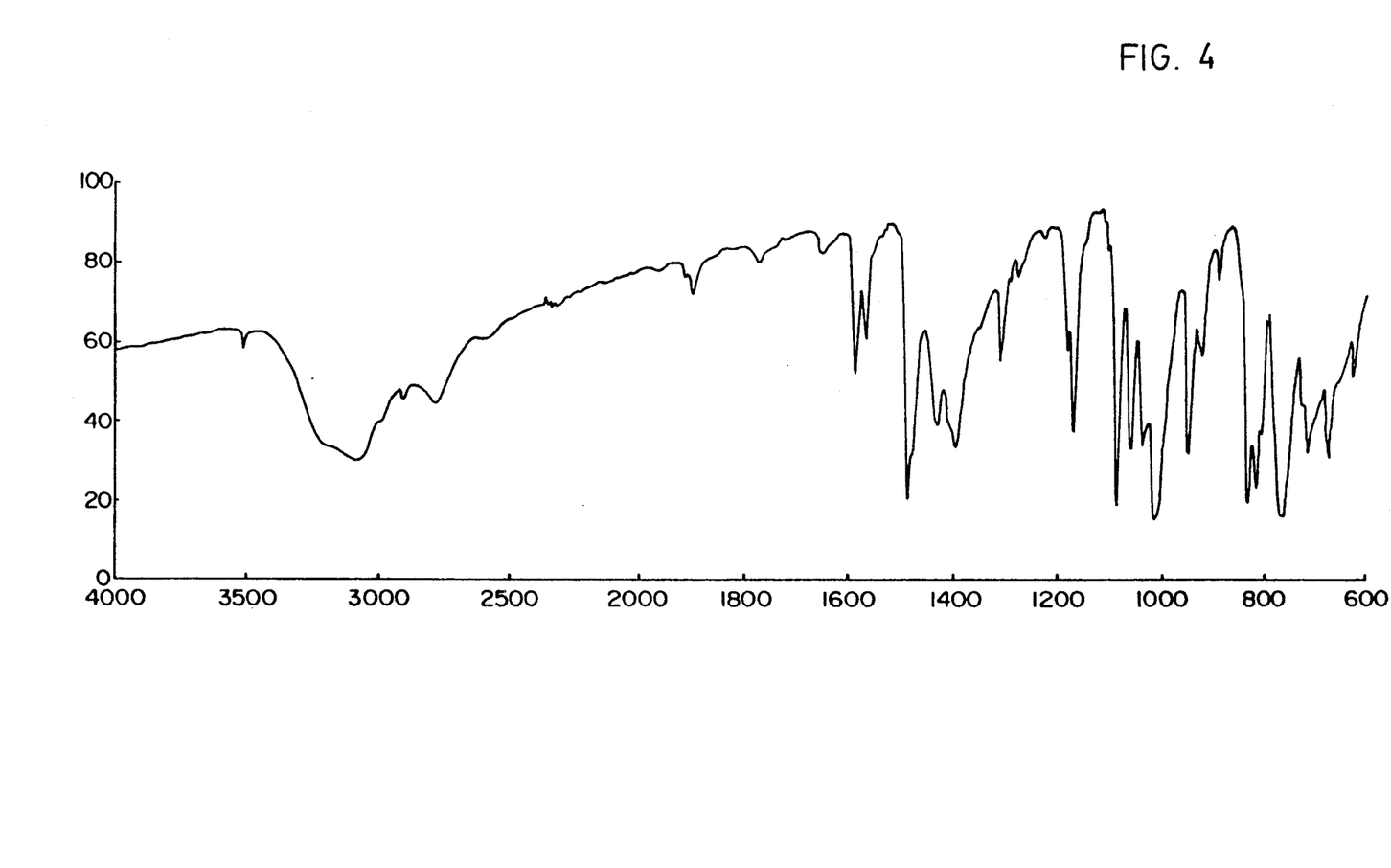
FIG. 4 is an IR spectrum of the addition compound formed by 1,1-bis(4-chlorophenyl)-2,2,2-trichloroethanol and dimethyl sulphoxide, the wavelengths in cm$^{-1}$ being given in abscissae and the transmittance in % being given in ordinates.
Figure 5:
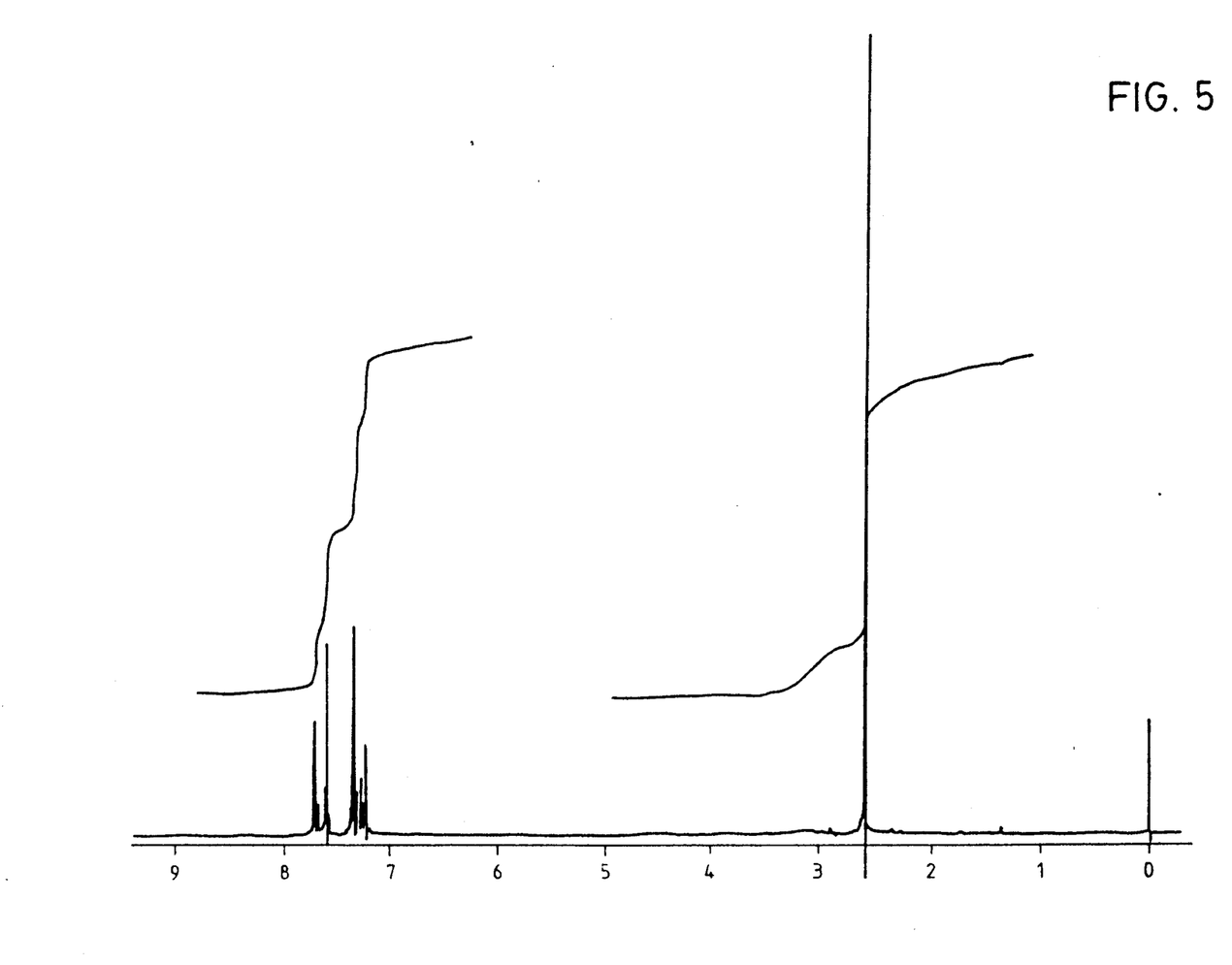
FIG. 5 is the proton NMR spectrum of said addition compound. In abscissae are given the chemical shifts relative to the tetramethyl silane reference in ppm and the radiation absorption intensity is given in ordinates.
Figure 6:
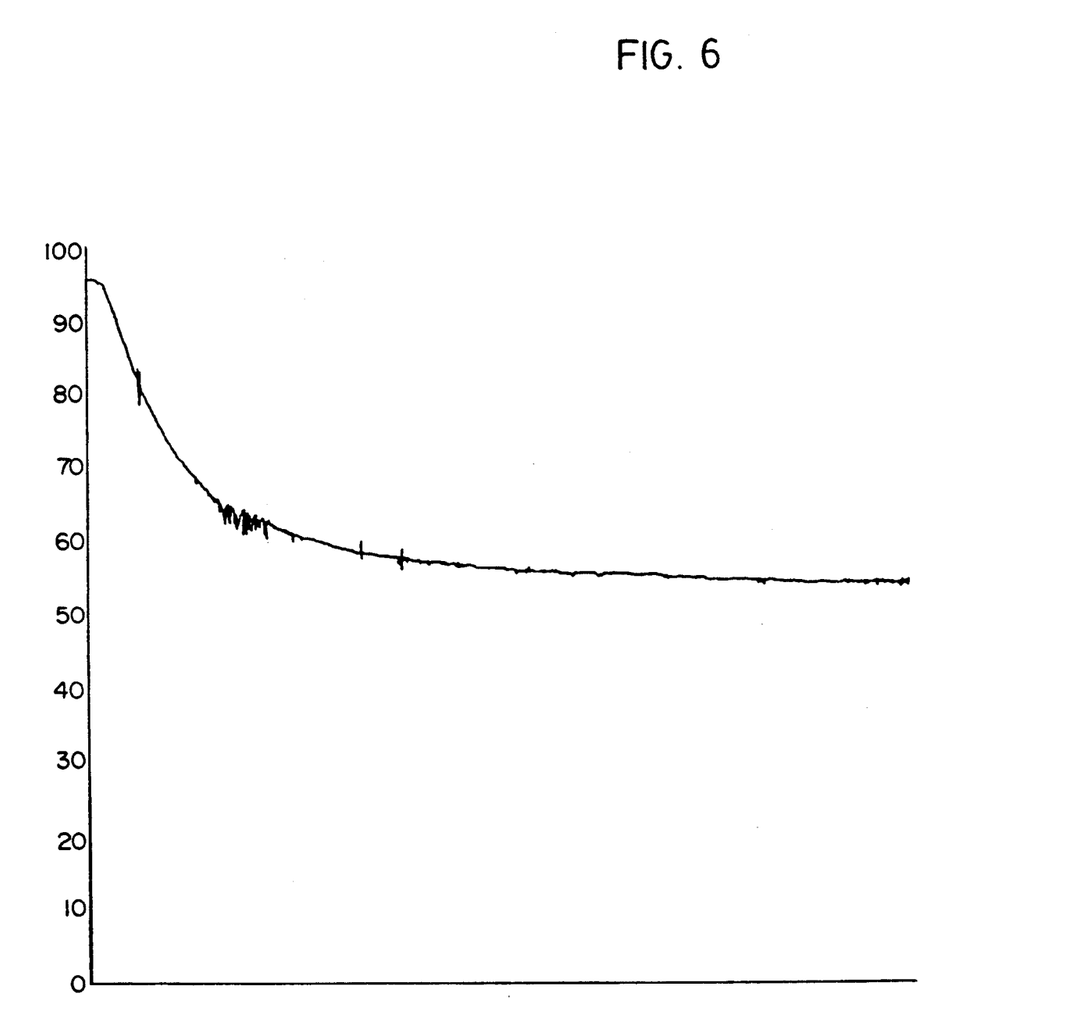
FIG. 6 is a thermogravimetric analysis of said addition compound. The relative weight of the sample (2 mg represent 100 on the scale) is given in ordinates, the variation in time, when held isothermally at 120° C. being recorded in abscissae (5 mm/min).

40.1 g of the addition compound were obtained (pure m.p. 93.0°–93.5° C. Elementary analysis (wt %) for $C_{16}H_{15}O_2Cl_5S$: Calculated: C, 42.83; H, 3.37; S, 7.15; Cl, 39.55; Found: C, 42.89 and 43.03; H3.21 and 3.20; S, 7.14 and 6.91; Cl, 39.67 and 39.81. IR (FIG. 4) and proton NMR (FIG. 6) spectra in conformity with the nature of the addition compound) which were dissolved in 400 g of xylene at room temperature. The solution was treated, also at room temperature, twice with 40 g of water.

The xylene was removed by distillation and 32.8 g of dicofol having a 97.8% p,p'-dicofol content, a recovery yield of 91.1% and a wt % composition: p,p'-DCBZ, 1.0; o,p'-dicofol, 1.1; p,p'-dicofol, 97.8; p,p'-ClDDT, 0.05; other DDT(R), <0.1, were obtained.

EXAMPLE 2

50.0 g of technical dicofol, having a p,p'-dicofol content of 70.5% (column 1, Table 2), were dissolved in 50 g of carbon tetrachloride. 9.0 g of dimethyl sulphoxide were added and the solution was allowed to crystallise with stirring and cooling to 0° C. It was filtered and washed with carbon tetrachloride.

31.8 g of the addition compound were obtained and were heated to 120° C. at a reduced pressure of 5 mm Hg with a gentle air flow. It was held under these conditions for 5 hours.

24.8 g of dicofol having a 98.1% p,p'-dicofol content, a 68.9% recovery yield and a wt % composition: p,p'-DCBZ, 1.0; o,p'-dicofol, 0.6; p,p'-dicofol, 98.1; DDT(R), <0.1, were obtained.

EXAMPLE 3

50.0 g of technical dicofol, having a p,p'-dicofol content of 70.5% (column 1, Table 2), were dissolved in 26.9 g of xylene. 9.0 g of dimethyl sulphoxide were added and the solution was heated for 1 hour at 60° C.

It was allowed to crystallise with stirring and cooling to −10° C. It was filtered and washed with xylene. 35.7 g of the addition compound were obtained and dissolved in 35 g of n-decane at 95° C. It was treated twice with 35 g of water at 95° C.

The n-decane was removed by distillation and 28.9 g of dicofol having a 98.1% p,p'-dicofol content, a 80.3% recovery yield and a wt % composition: p,p'-DCBZ, 1.1; o,p'-dicofol, 0.6; p,p'-dicofol, 98.1; DDT(R), <0.1, were obtained.

EXAMPLE 4

50.0 g of technical dicofol, having a p,p'-dicofol content of 70.5% (column 1, Table 2), were dissolved in 59.0 g of a mixture of 52.7 g of dimethyl sulphoxide and 6.3 g of water. The solution was heated for 1 hour at 60° C. and was allowed to crystallise with stirring and cooling to 0° C. It was filtered and washed with dimethyl sulphoxide-water.

46.9 g of the addition compound were obtained and heated to 95° C. and treated twice with 90 g of water at 95° C.

32.8 g of dicofol having a 93.4% p,p'-dicofol content, a recovery yield of 87.0% and a wt% composition: o,p'-DCBF, 0.1; o,p'-DCBZ, 0.3; p,p'-DCBF, 0.1; p,p'-DCBZ, 0.9; o,p'-dicofol, 4.7; p,p'-dicofol, 93.4; p,p'-ClDDT, 0.06; other DDT(R), <0.1, were obtained.

EXAMPLE 5

50.0 g of technical dicofol, having a p,p'-dicofol content of 70.5% (column 1, Table 2), were dissolved in a mixture of 25.0 g of monochlorobenzene and 30 g of hexane.

The solution was cooled to 0° C. and the precipitated p,p'-DCBZ was removed by filtration. The solution was heated to 30° C. and 9 g of dimethyl sulphoxide were added. It was heated for 1 hour at 60° C. It was allowed to crystallise with stirring and cooling to −10° C.

The mixture was filtered and washed in the filter with the monochlorobenzene-hexane mixture.

38.4 g of the addition compound were obtained and heated to 95° C. and treated twice with 80 g of water at 95° C.

31.6 g of dicofol having a 99–1% p,p'-dicofol content, a recovery yield of 89% and a wt% composition: p,p'-DCBZ, 0.2; o,p'-dicofol, 0.6; p,p'-dicofol, 99.1; DDT(R), <0.1, were obtained.

EXAMPLE 6

50.0 g of technical dicofol, having a p,p'-dicofol content of 70.5% (column 1, Table 2), were dissolved in 46.0 g of hexane. 12.5 g of cyclohexanone were added.

It was allowed to crystallise with stirring and cooling to 5° C. It was filtered and washed with 18.0 g of hexane. 36.7 g of the addition product were obtained (pure m.p. 56.0°–57.0° C. Elementary analysis (wt %) for $C_{20}H_{19}O_2Cl_5$: Calculated: C, 51.25; H, 4.09; Cl, 37.82; Found: C, 51.29 and 51.48; H 4.00 and 3.98; Cl, 38.08 and 38.13. IR and proton NMR spectra in conformity with the nature of the addition compound) which were heated to 120° C. under a reduced pressure of 2 mm Hg with a gentle air flow.

EXAMPLE 7

50.0 g of technical dicofol, having a p,p'-dicofol content of 70.5% (column 1, Table 2), were dissolved in 45.9 g of hexane. 9.1 g of pyridine were added.

It was allowed to crystallise with stirring and cooling to 20° C. It was filtered and washed with 20 g of hexane. 37.9 g of the addition compound were obtained (pure m.p. 81.8°–82.9° C. Elementary analysis (wt %) for $C_{19}H_{14}ONCl_5$: Calculated: C, 50.75; H, 3.14; N, 3.12; Cl, 39.42; Found: C, 50.72 and 50.69; H 3.04 and 3.09; N, 3.07 and 3.05; Cl, 39.63 and 39.56. IR and proton NMR spectra in conformity with the nature of the addition compound) which were dissolved in 37.9 g of monochlorobenzene and washed several times with 30.0 g of acidulated water until the pyridine was removed.

The monochlorobenzene was removed by distillation and 31.9 g of dicofol having a 96.9% p,p'-dicofol content, a recovery yield of 87.6% and a wt% composition: p,p'-DCBF, 0.1; p,p'-DCBZ, 1.8; o,p'-dicofol, 0.8; p,p'-dicofol, 96.9; p,p'-ClDDT, 0.2; other DDT(R), <0.1, were obtained.

EXAMPLE 8

50.0 g of technical dicofol, having a p,p'-dicofol content of 70.5% (column 1, Table 2), were dissolved in 49.7 g of hexane. 15.9 g of isophoron were added.

It was allowed to crystallise with stirring and cooling to 5° C. It was filtered and washed with 20.0 g of hexane.

41.1 g of the addition compound were obtained (pure m.p. 68.6°–69.5° C. Elementary analysis (wt %) for $C_{23}H_{23}O_2Cl_5$: Calculated: C, 54.30; H, 4.57; Cl, 34.84; Found: C, 54.34 and 54.43; H 4.54 and 4.56; Cl, 34.80 and 35.07. IR and proton NMR spectra in conformity with the nature of the addition compound) which were heated to 120° C. under a reduced pressure of 2 mm Hg with a gentle air flow.

30.8 g of dicofol having a 93.5% p,p'-dicofol content, a recovery yield of 81.5% and a wt% composition: o,p'-DCBF, 0.1; p,p'-DCBZ, 1.9; o,p'-dicofol, 3.8; p,p'-dicofol, 93.5; p,p'-ClDDT, 0.1; other DDT(R), <0.1, were obtained.

EXAMPLE 9

50.0 g of technical dicofol, having a p,p'-dicofol content of 70.5% (column 1, Table 2), were dissolved in 49.0 g of hexane. 7.2 g of glacial acetic acid were added.

It was allowed to crystallise with stirring and cooling to 7° C. It was filtered and washed with 11.3 g of hexane. 29.7 g of the addition compound were obtained (pure m.p. 57.4°–58.2° C. Elementary analysis (wt %) for $C_{16}H_{13}O_3Cl_5$: Calculated: C, 44.63; H, 3.05; Cl, 41.17; Found: C, 44.57 and 44.65; H 3.06 and 2.91; Cl, 41.64 and 41.73. IR and proton NMR spectra were in conformity with the nature of the addition compound) which were dissolved in 29.5 g of monochlorobenzene and washed with 30 g of water until the acetic acid was removed.

The monochlorobenzene was removed with distillation and 26.6 g of dicofol having a 95.9% p,p'-dicofol content, a recovery yield of 72.2% and a wt% composition: p,p'-DCBZ, 2.2; o,p'-dicofol, 1.7; p,p'-dicofol, 95.9; p,p'-ClDDT, 0.1; other DDT(R), <0.1, were obtained.

EXAMPLE 10

50.0 g of technical dicofol, having a p,p'-dicofol content of 70.5% (column 1, Table 2), were dissolved in 47.0 g of hexane and 10.1 g of 1,4-dioxane were added.

It was allowed to crystallise with stirring and cooling to 20° C. It was filtered and washed with 9.4 g of hexane. 13.0 g of the addition product were obtained (pure m.p. 70.6°–71.8° C. Elementary analysis (wt %) for $C_{32}H_{26}O_4Cl_{10}$: Calculated: C, 46.35; H, 3.17; Cl, 42.76; Found: C, 46.39 and 46.23; H 3.11 and 3.10; Cl, 42.70 and 42.64. IR and proton NMR spectra in conformity with the nature of the addition compound) which were dissolved in 12.9 g of monochlorobenzene and washed several times with 10 g of water.

The monochlorobenzene was removed with distillation and 12 g of dicofol having a 94.5% p,p'-dicofol content, a recovery yield of 31.9% and a wt% composition: p,p'-DCBZ, 4.0; o,p'-dicofol, 1.1; p,p'-dicofol, 94.5; p,p'-ClDDT, 0.3, were obtained.

EXAMPLE 11

50.0 g of technical dicofol, having a p,p'-dicofol content of 70.5% (column 1, Table 2), were dissolved in 49.0 g of hexane and 4.7 g of acetonitrile were added.

It was allowed to crystallise with stirring and cooling to 20° C.

It was filtered and washed with 20 g of hexane. 26.5 g of the addition product were obtained (m.p. unstable at room temperature) which were dissolved in 25 g of monochlorobenzene and washed twice with 15 g of water.

The monochlorobenzene was removed with distillation and 23.7 g of dicofol having a 90.8% p,p'-dicofol content, a recovery yield of 61.0% and a wt % composition: o,p'-DCBF, 0.1; o,p'-DCBZ, 0.6; p,p'-DCBF, 0.2; p,p'-DCBZ, 2.0; o,p'-dicofol, 5.2; p,p'-dicofol, 90.8; p,p'-ClDDT, 0.2; other DDT(R), 0.1, were obtained.

EXAMPLE 12

50.0 g of a mixture of the following composition in wt %: o,p'-DCBF, 0.1; o,p'-DCBZ, 0.2; p,p'-DCBF, 0.3; p,p'-DCBZ, 1.0; o,p'-dicofol, 0.5; p,p'-dicofol, 76.0; o,p'-DDE, 15.2; p,p'-DDE, <0.1; o,p'-ClDDT, 0.1; p,p'-ClDDT, 3.1; remainder, 3.4, were dissolved in a mixture of 31.8 g of monochlorobenzene and 31.8 g of n-decane. It was cooled to 0° C. and the p,p'-DCBZ which separated out was removed by filtration. It was heated to 30° C. and 11.3 g of water were added. It was cooled with vigorous stirring to 5° C. It was filtered and washed with 11.0 g of hexane.

24.0 g of the addition product were obtained (it was not possible to purify it satisfactorily for the precise identification thereof) having a 86.4% p,p'-dicofol content and 11.5% water.

The addition product melted at 80° C., the supernatant water was removed by decantation and the product was dried at 80° C. and 5 mm Hg. 21.6 g of dicofol having a 98.8% p,p'-dicofol content, a recovery yield of 55.9% and a wt % composition: p,p'-DCBZ, 0.3; p,p'-dicofol, 98.8; o,p'-DDE, 0.1; p,p'-ClDDT, 0.8, were obtained.

EXAMPLE 13

50 mg of the same mixture of the previous Example were dissolved in 31.8 g of monochlorobenzene and 31.8 g of n-decane. It was cooled to 0° C. and the p,p'-DCBZ which separated out was removed. It was heated to 30° C. and 4.1 g of dimethyl sulphoxide (0.52 mole of dimethyl sulphoxide/mole of p,p'-dicofol). were added.

It was allowed to crystallise with stirring and cooling to −10° C. It was filtered and washed with 8.5 g of a mixture of monochlorobenzene and n-decane. 39.6 g of the addition compound were obtained (pure m.p. 103.8°-104.7° C. Elementary analysis (wt %) for $C_{30}H_{24}O_3Cl_{10}S$: Calculated: C, 43.99; H, 2.96; S, 3.91; Cl, 43.28; Found: C, 44.12 and 44.09; H 2.94 and 2.93; S, 3.91 and 3.74; Cl, 43.66 and 43.53. IR and proton NMR spectra in conformity with the nature of the addition compound) which were dissolved in 17 g of monochlorobenzene and washed three times with 17 g of water.

The monochlorobenzene was removed by distillation and 34.2 g of dicofol having a 99.2% p,p'-dicofol content, a recovery yield of 91.3% and a wt % composition: p,p'-DCBZ, 0.5; p,p'-dicofol, 99.2; o,p'-DDE, 0.03; p,p'-ClDDT, 0.15, were obtained.

EXAMPLE 14

50.0 g of a mixture of the following composition in wt %: o,p'-DCBF, <0.1; o,p'-DCBZ, 0.2; p,p'-DCBF, 0.6; p,p'-DCBZ, 1.3; o,p'-dicofol, p,p'-dicofol, 74.0; o,p'-DDE, 17.6; p,p'-DDE, 0.2; o,p'-ClDDT, 0.1; p,p'-ClDDT, 3.0; remainder, 2.6, were dissolved in a mixture of 23.8 g of monochlorobenzene and 35.9 g of n-decane. It was cooled to 0° C. and the p,p'-DCBZ which separated out was removed by filtration. It was heated to 40° C. and 8.1 g of dimethyl sulphoxide were added.

It was allowed to crystallise and was cooled with stirring to −10° C. It was filtered and washed with 20.8 g of the same mixture of monochlorobenzene and n-decane. 44.0 g of the addition product were obtained, which were dissolved in 18.5 g of monochlorobenzene at 70° C. and washed 3 times with 18.5 g of water.

The monochlorobenzene was removed by distillation and 34.7 g of dicofol having a 99.5% p,p'-dicofol content, a recovery yield of 93.3% and a wt % composition: p,p'-DCBZ, 0.3; p,p'-dicofol, 99.5; DDT(R), <0.1, were obtained.

EXAMPLE 15

50.0 g of a mixture of the following composition in wt %: o,p'-DCBF, 0.1; o,p'-DCBZ, 0.3; p,p'-DCBF, 0.6; p,p'-DCBZ, 1.2; o,p'-dicofol, 2.2; p,p'-dicofol, 73.2; o,p'-DDE, 6.2; o,p'-DDT, 8,6; p,p'-DDE, 0.1; o,p'-ClDDT, 0.2; p,p'-ClDDT, 2.9; remainder, 4.4, were dissolved in a mixture of 29.5 g of monochlorobenzene and 29.5 g of n-decane. It was cooled to 0° C. and the p,p'-DCBZ which separated out was removed by filtration. It was heated to 30° C. and 8.4 g of dimethyl sulphoxide were added.

It was allowed to crystallise and was cooled with stirring to −10° C. It was filtered and washed with 15 g of the same mixture of monochlorobenzene and n-decane. 44.2 g of the addition product were obtained, which were dissolved in 20 g of monochlorobenzene at 70° C. and washed 3 times with 20 g of water.

The monochlorobenzene was removed by distillation and 34.1 g of dicofol having a 99.0% p,p'-dicofol content, a recovery yield of 92.1% and a wt % composition: p,p'-DCBZ, 0.5; p,p'-dicofol, 99.0; DDT(R), <0.1, were obtained.

EXAMPLE 16

50.0 g of technical dicofol (column 1, Table 2) were dissolved in a mixture of 29.5 g of monochlorobenzene and 29.5 g of n-decane. The solution was cooled to 0° C. and the p,p'-DCBZ which separated out was removed by filtration. The solution was heated to 30° C. and 9.0 g of dimethyl sulphoxide were added.

After being seeded with o,p'-dicofol, it was allowed to crystallise with stirring and cooling to −10° C. for an extended period of time. The mixture was filtered and washed with the same monochlorobenzene/n-decane mixture. 45 g of the addition product were obtained and were dissolved in 20 g of monochlorobenzene at 70° C. and washed three times with 20 g of water. The monochlorobenzene was removed by distillation and 67.5 g of dicofol having the following wt % composition: p,p'-DCBZ, 0.6; o,p'-dicofol, 9.3; p,p'-dicofol, 89.6; DDT(R), <0.1, were obtained.

EXAMPLE 17

60.0 g of a mixture of the following composition in wt %: o,p'-DCBF, 0.1; o,p'-DCBZ, 0.2; p,p'-DCBF, 0.6; p,p'-DCBZ, 1.4; o,p'-dicofol, 1.1; p,p'-dicofol, 73.9; o,p'-DDE, 17.6; p,p'-DDE, 0.2; o,p'-ClDDT, 0.1; p,p'-ClDDT, 3.0; remainder, 1.8, were dissolved in 60.0 g of n-decane at 60° C. 2.0 g of micronised silica as added followed by filtration at 60° C. 8.3 g of dimethyl sulphoxide were added slowly over 105.0 g of the filtered solution containing 37.0 g of p,p'-dicofol at 60° C. The addition compound starts to crystallise as from 60% of added dimethyl sulphoxide. It is cooled to 15° C., filtered and washed with 20.0 g of n-decane. 47.3 g of addition product were obtained, were dissolved in 20.0 g of monochlorobenzene and washed three times with 20.0 g of water.

The monochlorobenzene was removed by distillation and 36.3 g of dicofol having a 98.0% p,p'-dicofol content, a recovery yield of 97.5% and a wt % composition: p,p'-DCBZ, 1.9; p,p'-dicofol, 98.0; DDT(R), <0.1, were obtained.

By hot dissolution in an equal weight of isopropyl alcohol, cooling to 20° C., filtration and removal of the isopropyl alcohol, dicofol of the following wt % composition was obtained: p,p'-DCBZ, 0.2; p,p'-dicofol, 99.7; DDT(R), <0.1.

What we claim is:

1. A process for the preparation of 1,1-bis(4-clorophenyl)-2,2,2-trichloroenthanol starting out from a mixture containing 1,1-bis(4-chlorophenyl)-2,2,2-trichloroethanol together with at least one compound selected from a first group formed by 1-(4-chlorophenyl)-1-(2-chlorophenyl)-2,2,2-trichloroethanol, 1-(4-chlorophenyl)-1-(2-chlorophenyl)-2,2,2-trichloroethane and 1-(4-chlorophenyl)-1-(2-chlorophenyl)-2,2-dichloroethylene, characterised by forming an addition compound between 1,1-bis(4-chlorophenyl)-2,2,2-trichloroethanol and a second compound having an effective moderately electron donating functional group that is capable of interacting with the electrophilic hydrogen of the 1,1-bis(4-chlorophenyl)-2,2,2-tri-chloroethanol, isolating the addition compound and subsequently decomposing said addition compound.

2. The process of claim 1, wherein said second compound is selected from a second group which is dimethyl sulphoxide, cyclohexanone, isophoron, pyridine, 1,4-dioxane, acetic acid, acetonitrile or water.

3. The process of claim 1, comprising the steps of: a) forming a solution of said starting mixture in a solvent; b) adding said second compound to said solution to obtain a mass in which said addition compound is formed; c) cooling said mass and crystallisation of said addition compound; d) filtering and washing said addition compound and e) recovery of 1,1-bis(4-chlorophenyl)-2,2,2-trichloroethanol.

4. The process of claim 1, wherein said starting mixture is 1,1-bis(chlorophenyl)-2,2,2-trichloroethanol, also known as technical dicofol.

5. The process of claim 3, wherein in step c) 1-(4-chlorophenyl)-1-(2-chlorophenyl)-2,2,2-trichloroethanol is crystallised jointly with the crystallisation of said addition compound.

6. The process of claim 5, wherein crystal seeds of 1-(4-chlorophenyl)-1-(2-chlorophenyl)-2,2,2-trichloroethanol are provided to the mass to promote the crystallisation of this last named compound.

7. The process of claim 3, wherein said step a) solvent is an aromatic compound, a halogenated hydrocarbon, an aliphatic compound, mixtures thereof or a sulphur compound.

8. The process of claim 7, wherein said aromatic compound is xylene or monochlorobenzene.

9. The process of claim 7, wherein said halogenated hydrocarbon is carbon tetrachloride.

10. The process of claim 7, wherein said aliphatic compound is hexane or n-decane.

11. The process of claim 7, wherein said sulphur compound is aqueous dimethyl sulphoxide, said steps a) and b) being conducted simultaneously.

12. The process of claim 3, wherein steps a) and b) are conducted at temperatures ranging from 0° to 100° C. and steps c) and d) are conducted at temperatures ranging from −20° to 40° C.

13. The process of claim 12, wherein steps a) and b) are conducted at temperatures ranging from 20° to 60° C. and steps c) and d) are conducted at temperatures ranging from −10° to 20° C.

14. The process of claim 3, wherein said washing is effected with the same solvent as used in step a).

15. The process of claim 3, wherein said recovery is conducted by heating said addition compound to a temperature ranging from 20° to 140° C. under a reduced pressure of 1 to 300 mbar.

16. The process of claim 3, wherein said recovery is conducted by treating said addition compound with water at a temperature ranging from 80° to 100° C.

17. The process of claim 3, wherein said recovery is conducted by dissolving said addition compound in water inmiscible organic solvents, followed by washing with water.

18. The process of claim 17, wherein said organic solvent is removed by distillation.

19. A process for the preparation of addition compounds of 1,1-bis(4-chlorophenyl)-2,2,2-trichloroethanol starting out from a mixture containing 1,1-bis(4-chlorophenyl)-2,2,2-trichloroethanol together with at least one compound selected from a first group formed by 1-(4-chlorophenyl)-1-(2-chlorophenyl)-2,2,2-trichloroethanol, 1-(4-chlorophenyl)-1-(2-chlorophenyl)-2,2,2-trichloroethane and 1-(4-chlorophenyl)1-1(2-chlorophenyl)-2,2-dichloroethylene, characterised in that it comprises the steps of: a) forming a solution of said starting mixture in a solvent; b) adding to said solution a second compound having an effective moderately electron donating functional group capable of interacting with the electrophilic hydrogen of the 1,1-bis(4-chlorophenyl)-2,2,2-trichloroethanol to obtain a mass in which said addition compound is formed; c) cooling said mass and (crystallisation of) said addition compound; and d) filtering and washing said crystallizing addition compound.

20. The process of claim 19 wherein said second compound is selected from a second group which is dimethyl sulphoxide, cyclohexanone, isophoron, pyridine, 1,4-dioxane, acetic acid, acetonitrile or water.

21. Addition compound of 1,1-bis(4-chlorophenyl)-2,2,2-trichloroethanol having the formula where X is dimethyl sulphoxide, cyclohexanone, isophoron, pyridine, 1,4-dioxane, acetic acid, acetonitrile or water and n is 1 or 2 when X is dimethyl sulphoxide, n is 2 when X is 1,4-dioxane and n is 1 when X is cyclohexanone, isophoron, pyridine, acetic acid, acetonitrile and water.

22. The process for forming 1,1-bis(4-chlorophenyl)-2,2,2-trichloroethanol which comprises treating the compound of claim 21 with water.

23. The process according to claim 22, wherein the treatment is effected at a temperature ranging from 80° to 100° C.

24. The process according to claim 23, wherein the treatment is effected by dissolving said addition compound in a water immicible organic solvent, followed by washing with water.

25. The process according to claim 24, wherein said solvent is recovered by distillation.

26. A process of controlling mites on plants which comprises applying to said plant an acaricidal effective amount of the compound of claim 21.

27. A method for the preparation of 1,1-bis(4-chlorophenyl)-2,2,2-trichloroethanol which comprises heating the compound of claim 22.

28. A process for controlling mites on plants which comprises applying to said plant an acaricidal effective amount of a compound in any one of claims 1–17.

29. The process according to claim 27 wherein the heat treatment takes place at temperatures ranging from 20° to 140° C. at a pressure of 1-100 mbar.

30. The process for the preparation of 1,1-bis (4-chlorophenyl)-2,2,2-trichloroethaol starting out from a mixture containing 1,1-bis(4-chlorophenyl)-2,2,2-trichloroethanol together with at least one compound selected form a first group consisting of 1-(4-chlorophenyl)-1-(2-chlorophenyl)-2,2,2-trichloroethanol, 1-(4-chlorophenyl)-1-(2-chlorophenyl)-2,2,2-trichloroethane and 1-(4-chlorophenyl)-1-(2-chorophenyl)-2,2-dichloroethylene, characterised by forming an addition compound between 1,1-bis(4-chlorophenyl)-2,2,2-trichloroethanol and a second moderately electron donating compound selected from a second group consisting of halosubstituted alkyls, dialkyl ethers and cycloalkyl ethers containing up to 6 ring atoms and up to 2 oxygen ring atoms; alkyl ketones or cycloalkyl ketones containing up to 6 ring carbon atoms, whereby said ketone may be unsubstituted or substituted with alkyl groups; alkyl carboxylic acids; dialkyl sulfoxide; alkylnitrile or nitrogen containing heterocyclic ring containing up to 5 ring carbon atoms; isolating the addition compound and subsequently decomposing said addition compound.

31. A process for the preparation of 1,1-bis (4-chlorophenyl)-2,2,2-trichloroethanol starting out from a mixture containing 1,1-bis(chlorophenyl)-2,2,2-trichloroethanol together with at least one compound selected from a first group consisting of 1-(4-chlorophenyl)-1-(2-chlorophenyl)-2,2,2-trichloroethanol, 1-(4-chlorophenyl)-1-(2-chlorophenyl)-2,2,2-trichloroethane and 1-(4-chlorophenyl)-1-(2-chlorophenyl)-2,2-dichloroethylene, characterised by forming an addition compound between 1,1-bis(4-chlorophenyl)-2,2,2-trichloroethanol and a second moderately electron donating compound selected from a second group consisting of dimethyl sulfoxide, cyclohexane, isophoron, pyridine, 1,4-dioxane, acetic acid, acetonitrile and water; isolating the addition compound and subsequently decomposing said addition compound.

* * * * *

UNITED STATES PATENT AND TRADEMARK OFFICE
CERTIFICATE OF CORRECTION

PATENT NO. : 5,081,319

DATED : January 14, 1992

INVENTOR(S) : Jaime Palencia Adrubau, et al.

It is certified that error appears in the above-identified patent and that said Letters Patent is hereby corrected as shown below:

Column 7, line 4: "dicofol" should read as --dicofols--

Column 10, line 22: "CiDDT" should read as --ClDDT--

Column 12, lines 49-50: "clorophenyl" should read as --chlorophenyl--

Signed and Sealed this

Twenty-second Day of June, 1993

Attest:

MICHAEL K. KIRK

Attesting Officer     Acting Commissioner of Patents and Trademarks